United States Patent [19]

Herold et al.

[11] Patent Number: 5,058,770
[45] Date of Patent: Oct. 22, 1991

[54] CONTAINER FOR SUBSTANCES PREPARED BY MIXING COMPONENTS

[75] Inventors: Wolf-Dietrich Herold, Seefeld; Peter Koran, Weilheim; Helmut Pauser, Diessen, all of Fed. Rep. of Germany

[73] Assignee: THERA Patent GmbH & Co. KG Gesellschaft fuer industrielle Schutzrechte, Seefeld, Fed. Rep. of Germany

[21] Appl. No.: 538,329

[22] Filed: Jun. 15, 1990

[30] Foreign Application Priority Data

Jun. 15, 1989 [DE] Fed. Rep. of Germany ... 8907336[U]

[51] Int. Cl.⁵ ............................................. B67D 5/00
[52] U.S. Cl. .................................... 222/80; 222/136; 222/327
[58] Field of Search ................. 222/80, 327, 325, 386, 222/129, 135, 136, 137, 145; 206/222; 215/DIG. 8

[56] References Cited

U.S. PATENT DOCUMENTS

| | | | |
|---|---|---|---|
| 3,370,754 | 2/1968 | Cook et al. | 222/132 |
| 3,477,431 | 11/1969 | Walecka | 128/218 |
| 3,537,605 | 11/1970 | Solowey | 222/386 |
| 3,684,136 | 8/1972 | Baumann | 222/386 |
| 3,699,961 | 10/1972 | Szpur | 128/218 M |
| 3,885,710 | 5/1975 | Cohen | 222/145 |
| 4,201,316 | 5/1980 | Klingaman | 222/80 |
| 4,465,183 | 8/1984 | Saito et al. | 215/DIG. 8 |
| 4,648,532 | 3/1987 | Green | 222/386 |

FOREIGN PATENT DOCUMENTS

| | | |
|---|---|---|
| 1287251 | 3/1965 | Fed. Rep. of Germany . |
| 1939316 | 8/1969 | Fed. Rep. of Germany . |
| 2009403 | 2/1970 | Fed. Rep. of Germany . |
| 2060626 | 12/1970 | Fed. Rep. of Germany . |
| 3545614 | 12/1985 | Fed. Rep. of Germany . |
| 3715682 | 5/1987 | Fed. Rep. of Germany . |

Primary Examiner—Michael S. Huppert
Assistant Examiner—Anthoula Pomrening
Attorney, Agent, or Firm—Foley & Lardner

[57] ABSTRACT

A container for preparing a substance mixed from components which are initially separated comprises two chambers (54, 56) separated from each other by a partitioning structure (52). One chamber (54) holds a liquid component and is closed by a sheet (53) of plastics material, and the other chamber (56) holds a powdery component and forms a mixing chamber. An actuating member (58) is movably disposed within the partitioning structure (52). The actuating member (58) includes a seal (64, 66) which is locked in the rest and storage position of the container and is released when the actuating member is moved into its actuated position in which the sheet (53) is perforated. In the actuated position, the seal (64, 66) functions as a valve to permit the liquid component to enter the mixing chamber (56) while preventing parts of the mixture or components thereof from flowing back from the mixing chamber (56) into the first chamber (54).

9 Claims, 2 Drawing Sheets ived from its
CONTAINER FOR SUBSTANCES PREPARED BY MIXING COMPONENTS

BACKGROUND OF THE INVENTION

A container for preparing mixtures form two chemically interracting components, specifically a liquid and a powdery component, is known from German Auslegeschrift 1,287,251. The known container has two chambers which in its storage condition are sealed with respect to each other, each chamber holding one of the two components. For initiating the mixing process, a separating sheet provided between the two chambers is ruptured by pressure exerted on the liquid chamber, and continued pressure will displace the liquid from its chamber and transfer it to the chamber containing the powder where the mixing step proper is carried out by shaking the container.

Similar mixing containers are known from German Offenlegungsschriften 1,939,316, 2,009,403, 2,060,626 and 3,545,614.

U.S. Pat. No. 3,370,754 and German Offenlegungsschrift 3,715,682 disclose further devices in the form of two-chamber containers for mixing and dispensing substances, in which the partitioning between the chambers includes a valve element disposed in the wall of the mixing chamber.

Other mixing and dispensing devices for two-component substances are known from U.S. Pat. Nos. 3,885,710, 3,699,961, and 3,477,431. Each of these containers again includes some type of valve means for separating the two components in the storage condition.

The manufacturer provides the components in such quantities that the mixed substance exhibits optimum properties. If the mixing ratio is altered, these properties are deteriorated. This chance is not excluded with the known containers in view of the risk that an uncomplete reduction of the volume of the liquid chamber will result in the liquid being incompletely displaced into the mixing chamber or allow part of the liquid to flow back, during the mixing step, into the still existing volume of the liquid chamber.

A further problem with the known mixing containers resides in the fact that portions of the separating sheet may be included into the mixed substance.

SUMMARY OF THE INVENTION

It is an object of the invention to devise a container for substances that are prepared by mixing components with a high accuracy concerning the predetermined mixing ratio within the final substance.

To meet this object, the container of the present invention includes a first chamber for holding a first component, a second chamber for holding a second component and forming a mixing chamber, and partitioning means disposed between the chambers and sealing the chambers with respect to each other in the storage condition. For initiating a mixing phase, the partitioning means is actuable to permit the first component to be transferred to the mixing chamber. The partitioning means includes a valve disposed in a wall of the mixing chamber and being resiliently biassed in a closing direction that is opposite to the direction of transfer of the first component from the first chamber to the second chamber.

The container of the present invention is particularly suited for use in a combined centrifuging and mixing apparatus in which the first component is transferred to the mixing chamber by centrifugal forces exerted on the first component and directed towards the mixing chamber, and the subsequent mixing step is performed by reciprocating of the container. The considerable centrifugal forces occurring in the initial phase of operation of such apparatus can be used both to open the valve and to drive the first component into the mixing chamber without leaving a residue in the first chamber. Similarly, the acceleration forces acting on the mixed product in the subsequent reciprocation may be used for closing the valve so that the mixed product or components thereof are prevented from escaping from the mixing chamber. The closing and sealing function of the valve is assisted by the biasing force of the valve.

In a preferred embodiment, the valve includes a resilient gasket clamped in the partitioning means with its free peripheral portion cooperating with a sealing seat. A particularly secure sealing between the two chambers in the initial storage condition is achieved by a locking member which is adapted to be moved from a locking position in which it forces the periphery of the gasket against the sealing seat to a release position.

Preferably, the first and second chambers receive liquid and powdery components, respectively, such as components of a bone cement.

In the storage condition, the first chamber may be sealed by a separating sheet adapted to be perforated for initiating the mixing phase. A specifically easy handling of the container in causing the two chambers to communicate is achieved by a spike disposed on a structural member carrying the gasket and the sealing seat, which spike is adapted to be moved relatively to the locking member to perforate the separating sheet.

In a further preferred embodiment, the spike has a wall member partly surrounding a passage formed in the structural member, the outer surface of the wall member engaging, in the release position, a complementarily shaped surface portion provided in the first chamber. The separating sheet will thus be clamped in the region where it is perforated, thereby avoiding the risk of portions of the sheet to be included in the mixed substance.

According to a further preferred embodiment, a plunger serves to displace, in the release position, the separating sheet at a location remote from the area of perforation. This displacement of the separating sheet will cause the liquid to flow towards the perforated area due to the centrifugal forces referred to above.

For readily dispensing the mixed substance, the mixing chamber may have one end detachably mounted on the partitioning means and its opposite end closed by a piston.

BRIEF DESCRIPTION OF THE DRAWINGS

FIG. 3 showing the container under the influence of centrifugal forces bringing the two components together, FIG. 4 showing the condition during a mixing phase, and FIG. 5 illustrating a final compression phase.

DETAILED DESCRIPTION OF A PREFERRED EMBODIMENT

Figure 1:
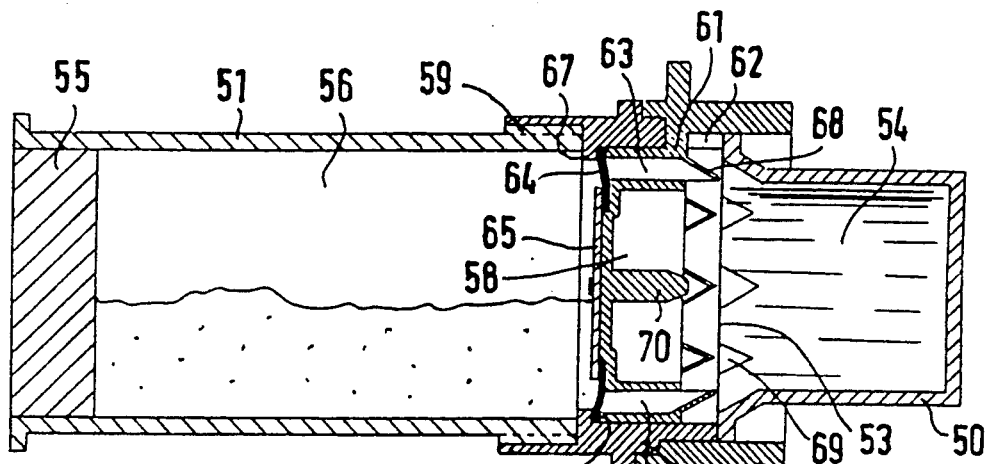
FIG. 1 is a sectional view taken along the axis of a two-chamber container, showing the container in a first, storage condition.

The container shown in FIG. 1 essentially consists of two cylindrical container portions 50, 51 and an intermediate partitioning structure 52. The container portion 50 is cup-shaped, with its end facing the partitioning structure 52 being closed by a separating sheet 53 of plastics material to form a first chamber 54 for holding a first component which may be liquid. The container portion 51 is tubular, with its end facing the partitioning structure 52 being open and its opposite end being closed by a movable piston 55. The container portion 51 forms a second chamber 56 for holding a second component which may be a powder. The second chamber 56 also forms the mixing chamber of the container.

The two components to be mixed may be specifically constituents of a bone cement, and the container described herein is particularly suited for preparing such a cement.

The partitioning structure 52 includes a cylindrical intermediate sleeve 57 and an actuating member 58 movable relative to the sleeve 57 in the axial direction of the container. The two ends of the sleeve 57 are joined to the container portions 50 and 51, the container portion 51 being connected by threads 59 so as to be detachable. In order to move the actuating member 58 relative to the sleeve 57, thus relative to the container portion 50, an outer ring 60 is provided which is connected to the actuating member by means of a plurality of circumferentially spaced webs 61. The webs 61 extend through axial slots 62 formed in the sleeve 57.

A plurality of circumferentially spaced axial passages 63 are provided in the substantially cup-shaped actuating member 58. The passages 63 are closed at their ends facing the mixing chamber 56 by an annular gasket 64 which is centrally clamped to the actuating member 58 by means of a retainer plate 65. In the storage condition shown in FIG. 1, the periphery of the gasket 64 is locked between a sealing seat 66 formed by the periphery of the actuating member 58 and an interior annular flange 67 of the sleeve 57 in a position in which the passages 63 are blocked.

At the end facing the container portion 50, each passage 63 terminates at the inner surface of a spike 68 which comprises a wall member having approximately the shape of a half hollow cone. Five spikes 68 are seen in the sectional view of FIG. 1, where the outer two spikes 68 are cut. A total of eight spikes 68 corresponding to eight passages 63 are equally spaced around the periphery of the actuating member 58.

In the storage condition shown in FIG. 1, the points of the spikes 68 spaced from the separating sheet 53. When the actuating member 58 is moved to the actuated position shown in FIG. 2 by operating the external ring 60—either manually or by means of a suitable appliance—the spikes 68 will perforate the sheet 53 and their semi-conical outer surfaces will engage in complementary semi-conical recesses 69 formed in the inner surface of the container portion 50. The sheet 53 will thereby be clamped and retained, in its areas of perforation, between the outer surfaces of the spikes 68 and the recesses 69, thereby maintaining the holes produced in the sheet open and at the same time preventing parts of the sheet from becoming loose and being included in the mixed substance.

Figure 2:
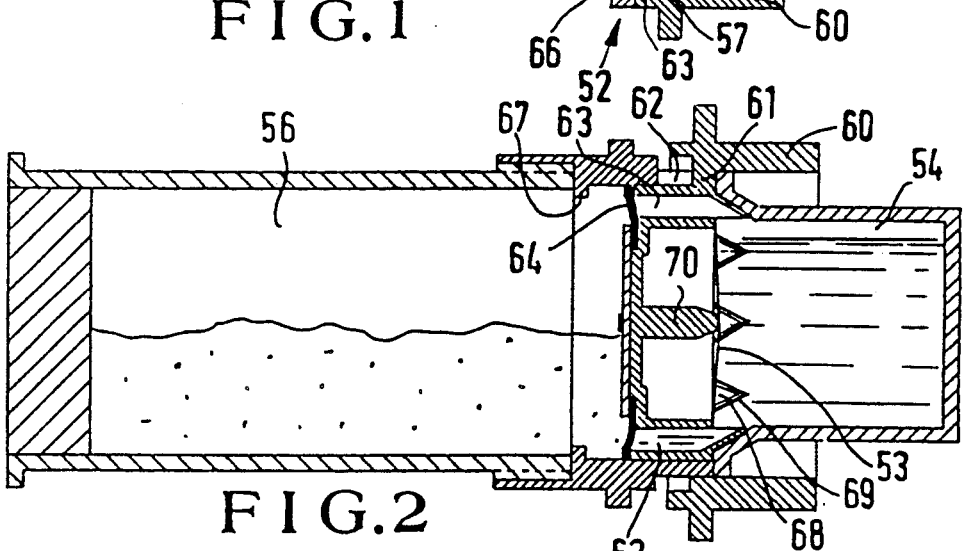
FIGS. 2 to 5 are sections similar to that of FIG. 1 but showing the container in a second, actuated condition, with FIG. 2 illustrating an intermediate position.

In the position shown in FIG. 2, the seal 64, 66 is still closed so that the components are still separated from each other. The thus achieved intermediate condition may be important for the handling in practice if there is a prolonged period of time between the actuating step described above and the subsequent mixing step, during which period the components must not react with each other. Therefore, the mixing process, which includes an initial step of transferring the liquid component to the mixing chamber 56 and a final compression step for degassing the mixed substance, and which is executed in the apparatus described further below, may be initiated immediately preceding the actual use of the substance, whereas all preparatory handling may be done long before.

In the actuated position shown in FIG. 2, a plunger 70 centrically provided on the actuating member 58 presses against the central portion of the sheet 53 and deflects it into the chamber 54. The sheet 53 is thereby deformed into a slightly conical overall shape which contributes to feeding the liquid towards the passages 63 under the influence of a force transferring the liquid to the mixing chamber 56. The plunger 70 also prevents the formation of a central depression in which a liquid residue might accumulate.

Figure 3:
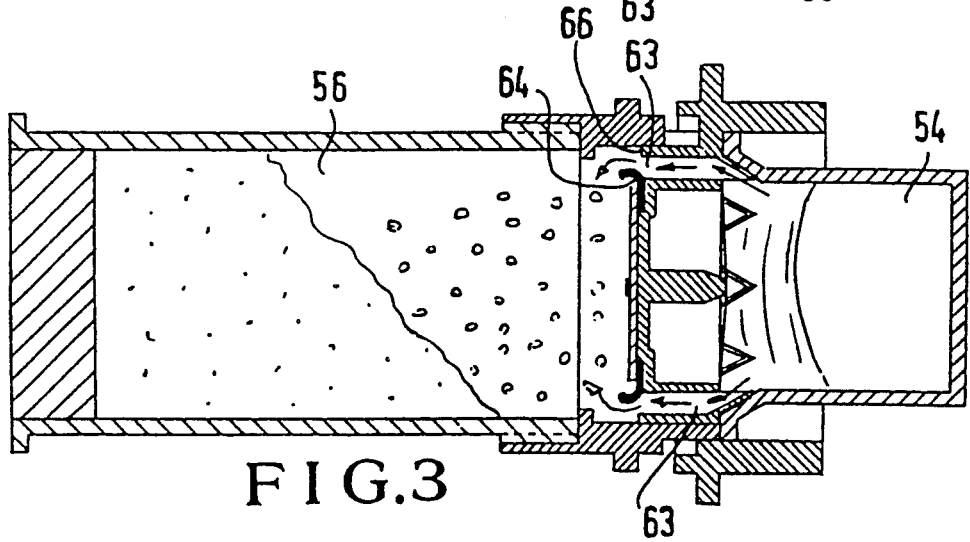

In the actuated condition illustrated in FIG. 2, the gasket 64 is resiliently biased against the sealing seat 66 to isolate the two chambers 54 and 56 from each other, even though the locking by the annular flange 67 was previously released. When an acceleration force now acts on the container from the right to the left according to FIG. 2, the gasket 64 will move away from the sealing seat 66 due to the force exerted on the liquid and the inertia of the gasket 64 itself. In this condition, the liquid will flow from the chamber 54 into the mixing chamber 56, as shown in FIG. 3.

Figure 4:
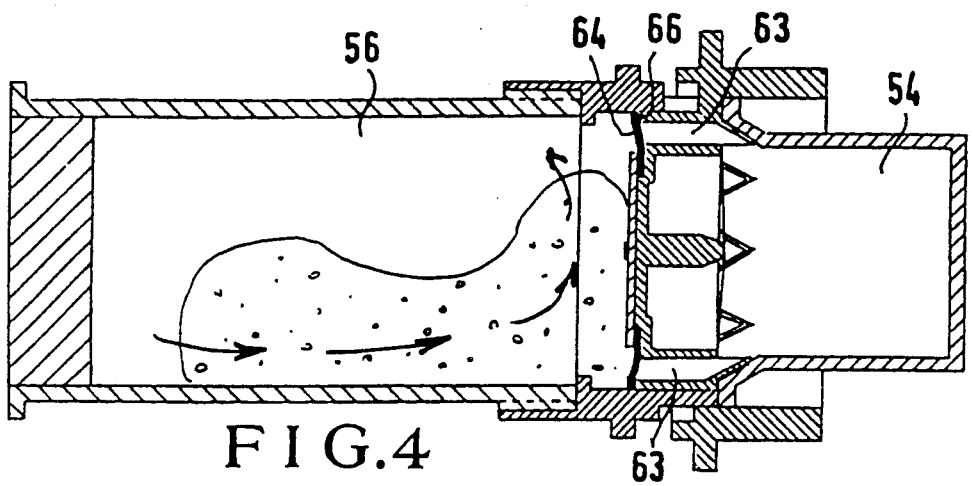

The container is subsequently subjected to a circular reciprocation due to which the two components perform a rolling or tumbling movement along the inner wall of the mixing chamber 56, as indicated by arrows in FIG. 4, and are thereby intimately mixed. During this reciprocation, the gasket 64 is forced by its bias against the sealing seat 66, and the sealing force is increased by the acceleration force which occurs whenever the mixture moves toward the sealing. A backflow of parts of the mixture or components thereof from the mixing chamber 56 to the chamber 54 is thereby prevented. The sealing 64, 66 disposed in the wall of the mixing chamber 56 thus functions as a valve means.

Figure 5:
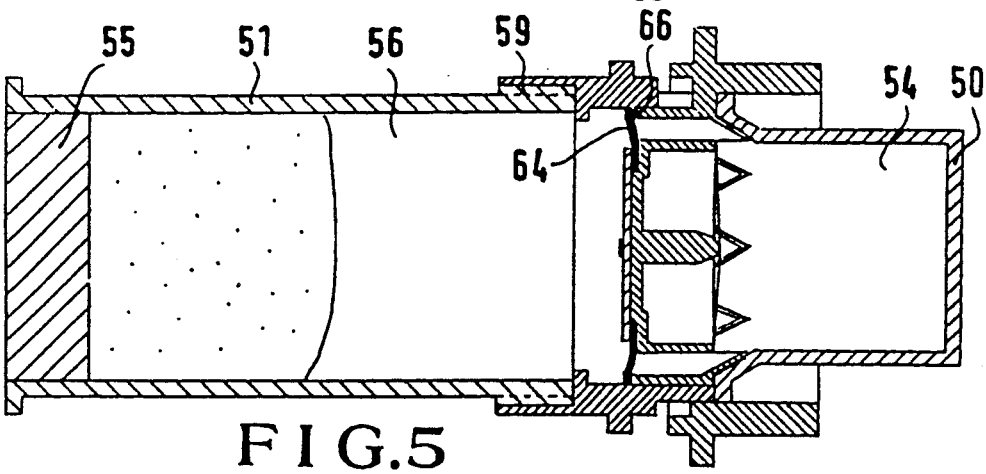

FIG. 5 finally illustrates a compression phase following the mixing phase, in which the container is again exposed to acceleration forces acting from the right to the left in FIG. 5 to compress the mixed substance on the piston 55, thereby removing any air that may have been included in the substance during the mixing step.

The container portion 51 may then be unscrewed from the partitioning structure 52 and inserted in a suitable appliance for advancing the piston 55 to dispense the mixture.

Figure 6:
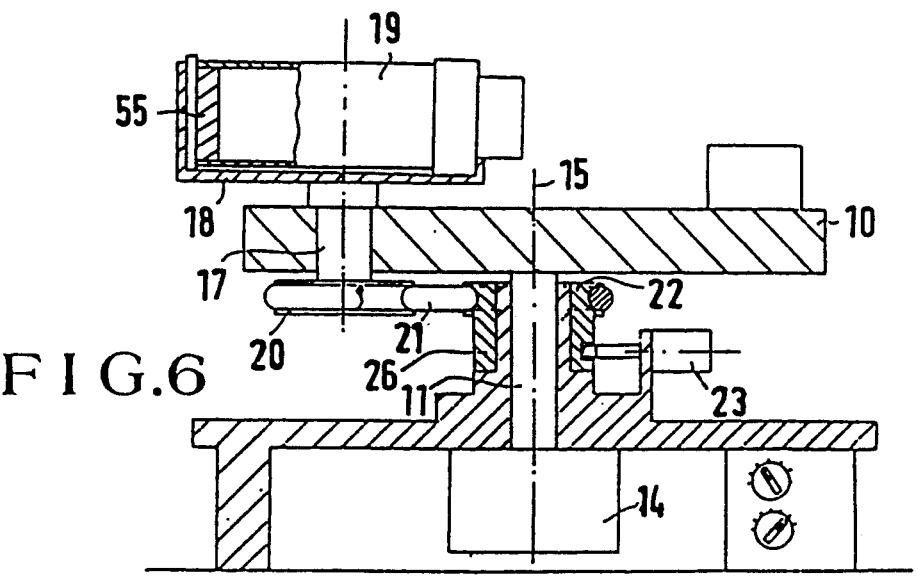
FIG. 6 is the schematic representation of a centrifuging and mixing apparatus as is particularly suited for executing the various operating phases illustrated in FIGS. 3 to 5.

The centrifuging and mixing apparatus shown in FIG. 6 includes a rotor 10 driven via a shaft 11 by a motor 14, the rotor 10 carrying, on an eccentric shaft 17, a mount 18 for receiving a container as shown in FIGS. 1 to 5. In FIG. 6, the container is identified by reference number 19. A pulley 20 is mounted on the eccentric shaft 17 and coupled via a belt 21 to a pulley 22 rotatably mounted about the axis 15 of the rotor shaft 11. A clutch 23 cooperates with a downwardly extended sleeve 26 of the pulley 22.

When the clutch 23 is disengaged, the container 19 is permitted to adjust itself to a fixed orientation relative to the rotor 10 in which the piston 55 is located at the radially outermost end. In this orientation, the container 19 is exposed solely to centrifugal forces which represent the above acceleration forces from the right to the left and serve to transfer the liquid component from the chamber 54 to the mixing chamber 56 according to FIG. 3 and, subsequent to the mixing phase, perform the compression step according to FIG. 5.

On the other hand, if the clutch 23 is engaged as shown in FIG. 6, the sleeve 26 and thus the pulley 22 are held stationary so that continued rotation of the rotor 10 will now rotate the container 19 about the axis of the shaft 17. This results in the circulating reciprocation required for the mixing step according to FIG. 4. The clutch 23 may be engaged and disengaged during rotation, so that the phases of operation explained in connection with FIGS. 3 to 5 may follow each other immediately.

As should be clear from the above description, once the container has been actuated, the further handling is done automatically by means of the centrifuging and mixing apparatus of FIG. 6 until the substance is ready for use.

What is claimed is:

1. A container for substances to be prepared by mixing components, comprising
    a first chamber for holding a first component, a second chamber for holding a second component and forming a mixing chamber,
    a partitioning means disposed between said chambers for sealing the chambers against each other in a storage condition of the container, the partitioning means being operable for initiating a mixing phase so as to permit said first component to be transferred to said mixing chamber, and
    valve means disposed in a wall of said mixing chamber, said valve means being resiliently biased in its closing direction opposite to the direction of transfer of said first component from said first chamber to said second chamber, said valve means including a resilient gasket clamped to said partitioning means and having a free peripheral portion for engaging a sealing seat.

2. The container of claim 1, including locking means relatively movable with respect to said sealing seat from a locking position held in said storage condition, in which said locking means presses the peripheral portion of said gasket against said sealing seat, to a release position.

3. The container of claim 2, wherein said first chamber in said storage condition is closed by a separating sheet which is adapted to be perforated for initiating said mixing phase.

4. The container of claim 3, wherein said partitioning means includes a spike for perforating said sheet, the spike being disposed on a structural part which carries said gasket and sealing seat and is movable with said structural part relative to said locking means and said sheet.

5. The container of claim 4, wherein said spike includes a wall member partly surrounding a passage in said structural part, the outer surface of said wall member engaging, in said release position, a complementary surface portion provided in said first chamber.

6. The container of claim 5, characterized in that the structural part includes a plunger for deflecting, in said release position, a portion of said sheet at a position remote from the area of perforation, into said first chamber.

7. The container of claim 1, wherein said mixing chamber has its one end detachably connected to said partitioning means and its opposite end closed by a piston for dispensing the mixed substance.

8. The container of claim 1, wherein said first chamber and said second chamber are adapted to hold a liquid and a powdery component, respectively.

9. The container of claim 8, wherein said components are components of a bone cement.

* * * * *